United States Patent [19]
Mills, Jr. et al.

[11] Patent Number: 6,083,726
[45] Date of Patent: Jul. 4, 2000

[54] METHODS FOR POLYNUCLEOTIDE SYNTHESIS AND ARTICLES FOR POLYNUCLEOTIDE HYBRIDIZATION

[75] Inventors: Allen P. Mills, Jr., Chatham; Bernard Yurke, Plainfield, both of N.J.

[73] Assignee: Lucent Technologies, Inc., Holmdel, N.J.

[21] Appl. No.: 09/018,248

[22] Filed: Feb. 3, 1998

[51] Int. Cl.$^7$ .............. C12P 19/34; C12Q 1/68; C07H 21/02
[52] U.S. Cl. ............ 435/91.1; 435/6; 435/91.2; 435/91.21; 536/23.1; 536/24.3; 536/24.31; 536/24.32; 536/24.33
[58] Field of Search .............. 435/6, 91.1, 91.2, 435/91.21; 536/231, 24.3, 24.31, 24.32, 24.33

[56] References Cited

U.S. PATENT DOCUMENTS 5,650,302 7/1997 Richards et al. ............. 435/91.2
5,795,714 8/1998 Cantor et al. .................. 435/6

OTHER PUBLICATIONS

Brown, David, "DNA–Encoded Chips Appear to Speed Tests for Genetic Mutations," The Washington Post, Nov. 24, 1997.
Mirkin, Chad A., et al., Nature 382:607–609 (1996).
Pease, Ann Caviani, et al, Proc. Natl. Acad. Sci. 91:5022–5026 (1994).
McGall, Glenn H., et al., J. of the Amer. Chem. Soc. 119(22):5082–5090 (1997).
Luo et al, "Improving the fidelity of Thermus thermophilus DNA ligase", Nucleic Acids Research 24(14):3071–3078, 1996.
Deng et al, "Basis for selection of improved carbohydrate binding single chain antibodies from synthetic gene libraries", Proc. Natl. Acad. Sci. 92:4992–4996, May 1995.

*Primary Examiner*—Jeffrey Fredman
*Attorney, Agent, or Firm*—Venable; John W. Schneller

[57] ABSTRACT

This invention relates to methods for making polynucleotides of any desired nucleotide sequence by repeating a series of reactions involving assembly of overlapping oligomers, ligation by DNA ligase, and cleavage with a restriction enzyme that cuts so as to add one or more additional nucleotides to a growing polynucleotide. This invention also relates to combining such a method for polynucleotide synthesis with a step employing localized melting of hybridized DNA oligomers, to synthesize an array of polynucleotides of different, defined nucleotide sequence on a substrate, and to the articles for polynucleotide hybridization so made. This invention further includes methods in which a substrate bearing an array of polynucleotides made according to the invention is used to determine the nucleotide sequence of a nucleic acid, or to detect or isolate a nucleic acid having a selected nucleotide sequence, and a device which analyzes a substrate-bound array of polynucleotides made according to the invention to determine the nucleotide sequence of a nucleic acid, or to detect or isolate a nucleic acid having a selected nucleotide sequence.

28 Claims, 2 Drawing Sheets

METHODS FOR POLYNUCLEOTIDE SYNTHESIS AND ARTICLES FOR POLYNUCLEOTIDE HYBRIDIZATION

FIELD OF THE INVENTION

The present invention pertains, in general, to methods of making polynucleotides of any desired nucleotide sequence, to methods of making polynucleotide hybridization probe arrays, and to articles for polynucleotide hybridization made by such methods. In particular, the present invention pertains to deoxyribonucleic acid (DNA) synthesis methods which use assembly of overlapping oligomers, ligation by DNA ligase, and cleavage with a restriction enzyme that cuts so as to add one or more additional nucleotides to a growing polynucleotide. The present invention further pertains to using such DNA synthesis methods, and employing localized melting of hybridized DNA oligomers, to synthesize an array of different polynucleotides of defined nucleotide sequence on a substrate, and to the articles for polynucleotide hybridization made therefrom.

BACKGROUND OF THE INVENTION

All publications and patent applications herein are incorporated by reference to the same extent as if each individual publication or patent application was specifically and individually indicated to be incorporated by reference.

The hybridization of single-stranded DNA and RNA to complementary immobilized probe strands is being used for detection of known sequences associated with pathogens and mutations. The immobilization of biological polymers on solid supports has also had significant impact on drug discovery and medical diagnostic methods. By using an array of different immobilized probe DNA strands, one may search for many types of DNA or RNA in parallel or determine the entire sequence of a single long strand of DNA or RNA [1–5]. U.S. Pat. No. 5,143,854 [15] describes the large scale photolithographic solid phase synthesis of polypeptides. The polypeptide arrays are synthesized on a substrate by attaching photo-removable groups to the surface of a substrate, exposing selected regions of the substrate to light to activate those regions, and attaching an amino acid monomer with a photo-removable group to the attached regions. The steps of activation and attachment can be repeated until polypeptides of desired length and sequences are synthesized. U.S. Pat. No. 5,412,087 [8] describes substrates with surfaces comprising compounds with thiol functional groups at one end, and protected at the other end with a photo-removable protecting group which can be used to construct arrays of immobilized anti-ligands, such as oligonucleotide probes or other biological polymers. A commercially available product (offered by Affymetrix, 3380 Central Expressway, Santa Clara, Calif. 95051) is made by the light-directed synthesis of DNA [6–9]. According to the current state of the art pertaining to the synthesis of polynucleotide arrays, there is only a 92–94% chance that a new nucleotide will be incorporated where desired [16]. Current technology thus imposes certain constraints on the possible array configuration, such as the practical upper limit on the number of nucleotides being approximately ten.

Presented here is a novel method for making DNA molecules of desired nucleotide sequence, and an alternate, more efficient method for the synthesis of DNA arrays which utilizes local melting of hybridized DNA rather than photochemistry to achieve a known pattern of DNA strands. Using the methods of this invention, one skilled in the art will be able to make DNA hybridization probes with longer nucleotide strands and with greater fidelity than is now available using current technology. One possible advantage of longer strands would be the stable hybridization of target strands to the hybridization array at room temperature. This would permit the use of annealing cycles for the purpose of improving the fidelity of the hybridization.

SUMMARY OF THE INVENTION

This invention comprises methods of making polynucleotides, of making polynucleotide hybridization probe arrays, the articles for polynucleotide hybridization made by such methods, methods wherein articles for polynucleotide hybridization made by the disclosed methods are used to detect or isolate nucleic acid molecules of selected nucleotide sequence, and devices in which articles for polynucleotide hybridization made by the disclosed methods are analyzed in the determination of the nucleotide sequence of a nucleic acid, or in the detection or isolation of nucleic acid molecules of selected nucleotide. More specifically, the present invention provides non-photochemical methods of making DNA, and of making DNA hybridization probe arrays. Even more specifically, the present invention provides methods of making DNA hybridization probe arrays which use local melting of hybridized DNA, DNA ligase, and a restriction enzyme, rather than photochemistry, to achieve an ordered array of DNA strands of varying nucleotide sequence which are bound to a substrate in a known pattern.

The methods of the present invention can be used to create sources of nucleotide diversity useful in screening for biological activity. Thus, the methods and articles of the present invention will find application wherever polynucleotide analysis is necessary, such as for mutation analysis, polymorphism determinations, clinical studies, and drug design. Fields of study for which the methods and articles of the present invention will find application include those utilizing polynucleotide hybridization such as enzymology, microbiology, immunology, forensic analyses, and pathology.

In addition, the methods of the present invention provide DNA hybridization probe arrays which will be useful in the newly-emerging field of DNA-based computers. DNA computers solve combinatorial problems through molecular computation [14].

The DNA hybridization plates of the present invention can be exposed to unknown DNA and then allowed to hybridize with fluorescent-labeled molecules or exposed to dyes, such as ethidium bromide, which are specific to double-stranded DNA. Pertinent calculations can be made using any algorithm-based read-out device based on either the intensity of the fluorescence recorded from each spot, the sequence excitation detected using lasers, or based on flooded-area detection. Accordingly, the present invention includes methods wherein a substrate comprising a DNA hybridization probe array is made by the techniques disclosed herein, is incubated with nucleic acid molecules of interest, and is analyzed using a device that detects double-stranded complexes comprising hybridized nucleic acids on the substrate, e.g. by detection of fluorescence, so as to identify the presence of hybridizing nucleic acids in the set of nucleic acid molecules of interest. The present invention also includes a device for detecting substrate-bound double-stranded nucleic acid complexes, wherein the device comprises a substrate to which is bound a DNA hybridization probe array made according to the methods disclosed herein, and a means for detecting labeled double-stranded nucleic acid hybridization complexes bound to one or more sites on the surface of the substrate; e.g. a fluorescent read-out device which performs computerized analysis of fluorescent intensities. The identification of double-stranded hybridization complexes formed by base-pairing of a nucleic acid to a specific set of substrate-bound polynucleotides of known sequence permits determination of the nucleotide sequence of the bound nucleic acid [7]. The substrate can be heated to release the detected nucleic acid molecules of interest from the DNA hybridization probe array, e.g., for subcloning or PCR amplification.

One skilled in the art can easily make any necessary adjustments in accordance with the necessities of the particular situation. For example, one skilled in the art could easily substitute RNA or polynucleotides comprising chemical analogs of ribonucleotides, such as 2'-O-alkyl- or 2'-O-aryl-ribonucleotides, for increased hybridization affinity and resistance to degradation by nucleases, in the described methods, articles and examples of the present invention. Alternatively, one skilled in the art could easily substitute polynucleotides comprising modified internucleotide linkages such as phosphorothioate, methylphosphonate, etc., or polynucleotides comprising chemical analogs of nucleotides or base-pairing, non-nucleotide subunits, such as protein nucleic acid (PNA) subunits, for altered hybridization affinity and/or for resistance to degradation by nucleases, in successfully making and using the present invention. Further objects and advantages of the present invention will be clear from the description that follows.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The brief summary of DNA and RNA which follows is not meant to be exhaustive of the subject, but merely to provide a general framework for understanding the present invention. A more complete description of DNA and RNA technology is available in a number of texts, including: J. D. Wilson, M. Gilman, J. Witkowski, and M. Zoller, 1992, "Recombinant DNA", Second Edition, Scientific American Books; and, B. Lewin, 1997, "Genes VI", Oxford University Press. Each of these general texts are herein incorporated by reference.

As set forth above, the present invention is directed to alternative methods of making nucleic acid hybridization probe arrays. A nucleotide is one of the monomeric units from which DNA or RNA polymers are constructed. In general, polynucleotides are linear sequences of many nucleotides (the Greek-derived prefix poly- indicates "many"), while linear sequences of a few nucleotides are called oligonucleotides (the Greek-derived prefix oligo- indicates "a few"). The choice of whether to refer to a nucleic acid of a given number of nucleotide subunits as a polynucleotide or as an oligonucleotide is arbitrary. Oligomers are linear sequences of relatively few nucleotides. A number followed by the suffix -mer refers to an oligomer of the indicated number of nucleotide subunits. For example, an oligomer that contains 12 or 17 bases is referred to as a 12-mer or as a 17-mer, respectively. Each nucleotide contains a phosphate group, a sugar moiety, and either a purine or pyrimidine base. The sugar of DNA is deoxyribose while the sugar of RNA is ribose. Nucleosides consist of a purine or pyrimidine base attached to ribose or deoxyribose. Polynucleotides and oligonucleotides each consist of a linear sequence of nucleotides of DNA or RNA in which the 3' position of the sugar of one nucleotide is linked through a phosphate group to the 5' position of the sugar on the adjacent nucleotide. Ligation is the formation of the phosphodiester bond which joins the adjacent nucleotides in the same nucleic acid chain. Two purine bases and two pyrimidine bases are found in both DNA and RNA. The purines adenine (A) and guanine (G) and the pyrimidine cytosine (C) occur in both DNA and RNA. However, thymine (T) only occurs in DNA and uracil (U) only occurs in RNA. The nucleotides of DNA are deoxyadenylic acid, thymidylic acid, deoxyguanilic acid, and deoxycytidylic acid, while the corresponding nucleotides of RNA are adenylic acid, uridylic acid, guanylic acid, and cytidylic acid. The sugar-phosphate backbones are on the outside of the DNA molecule and the purine and pyrimidine bases are on the inside, oriented in such a way that they can form hydrogen bonds to bases on opposing chains. Adenine (A) can pair only with thymine (T), while guanine (G) can bond only with cytosine (C). Hybridization is the process by which two complementary RNA and DNA strands pair to produce an RNA-DNA hybrid, or by which two complementary DNA single strands pair to produce a DNA-DNA hybrid, also known as double-stranded DNA. Universal base analogues or universal nucleotides are capable of hybridizing with any one of the four DNA nucleotides [10,11]. An example of a universal base analogue is 5-Nitroindole [11].

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, e.g., J. Sambrook, E. F. Fritsch, and T. Maniatis, 1989, Molecular Cloning: A Laboratory Manual, Second Edition, Books 1–3, Cold Spring Harbor Laboratory Press; B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts are herein incorporated by reference.

Methods in which a substrate-bound polynucleotide hybridization probe array made according to the methods disclosed herein is employed to detect or isolate nucleic acid molecules comprising selected nucleotide sequences require that substrate-bound polynucleotides comprise a nucleotide sequence that is complementary to a nucleotide sequence in the nucleic acid to be detected or isolated. One skilled in the art would recognize that the number of consecutive complementary nucleotides that must be present in the substrate-bound polynucleotides so that they hybridize specifically to nucleic acid molecules comprising said selected nucleotide sequences can vary considerably, from 4 or five up to 14 or more, depending on such factors as the complexity of the solution of nucleic acids comprising the molecules to be detected or isolated, and the physical conditions (ionic strength, temperature, anionic reagents, etc.) used in the hybridization and wash steps. The statement that a nucleic acid molecule hybridizes specifically to a substrate-bound polynucleotide is intended to mean that a portion of the nucleic acid molecule comprising a nucleotide sequence complementary to a sequence in a substrate-bound polynucleotide binds by Watson-Crick base-pairing to the complementary portion of the substrate-bound polynucleotide to form a stable double-stranded complex, under hybridization conditions that are sufficiently stringent that nucleic acid molecules having fewer bases complementary to, or forming less stable duplex structures with, said substrate-bound polynucleotides do not bind said substrate-bound polynucleotides and form stable double-stranded complexes. Selection of parameters such as the lengths of the complementary portions of the substrate-bound polynucleotides and the conditions used in hybridization and wash steps, so that a nucleic acid molecule hybridizes specifically to a substrate-bound polynucleotide, is well within the capabilities of a person of ordinary skill in the art (see, for example, see J. Sambrook et al., 1989, Molecular Cloning: A Laboratory Manual, Second Edition, Chapter 11, Cold Spring Harbor Laboratory Press.

Our goals in developing the methods of the present invention were to provide alternate methods of making DNA polynucleotides of defined sequence, and to provide faster, alternate methods of fabricating DNA hybridization probe arrays which do not utilize photochemistry. Photochemistry-based methods of producing DNA hybridization probes involve energetic photons which can introduce unwanted pathways with unforseen excitations. In contrast, the methods of the present invention involve more predictable, less harsh conditions which rely on very specific Crick-Watson DNA pairing and controlled heating of pre-designated areas. In producing arrays of DNA hybridization probes, the use of localized heating with selected temperatures provides a level of control not presently available in the current technology. The methods of the present invention can be used to produce articles for DNA hybridization which have longer nucleotide strands and greater fidelity than DNA hybridization articles which are currently available. Exemplary methods are outlined in FIGS. 1 and 2 and described herein.

MATERIALS AND METHODS

Figure 1:
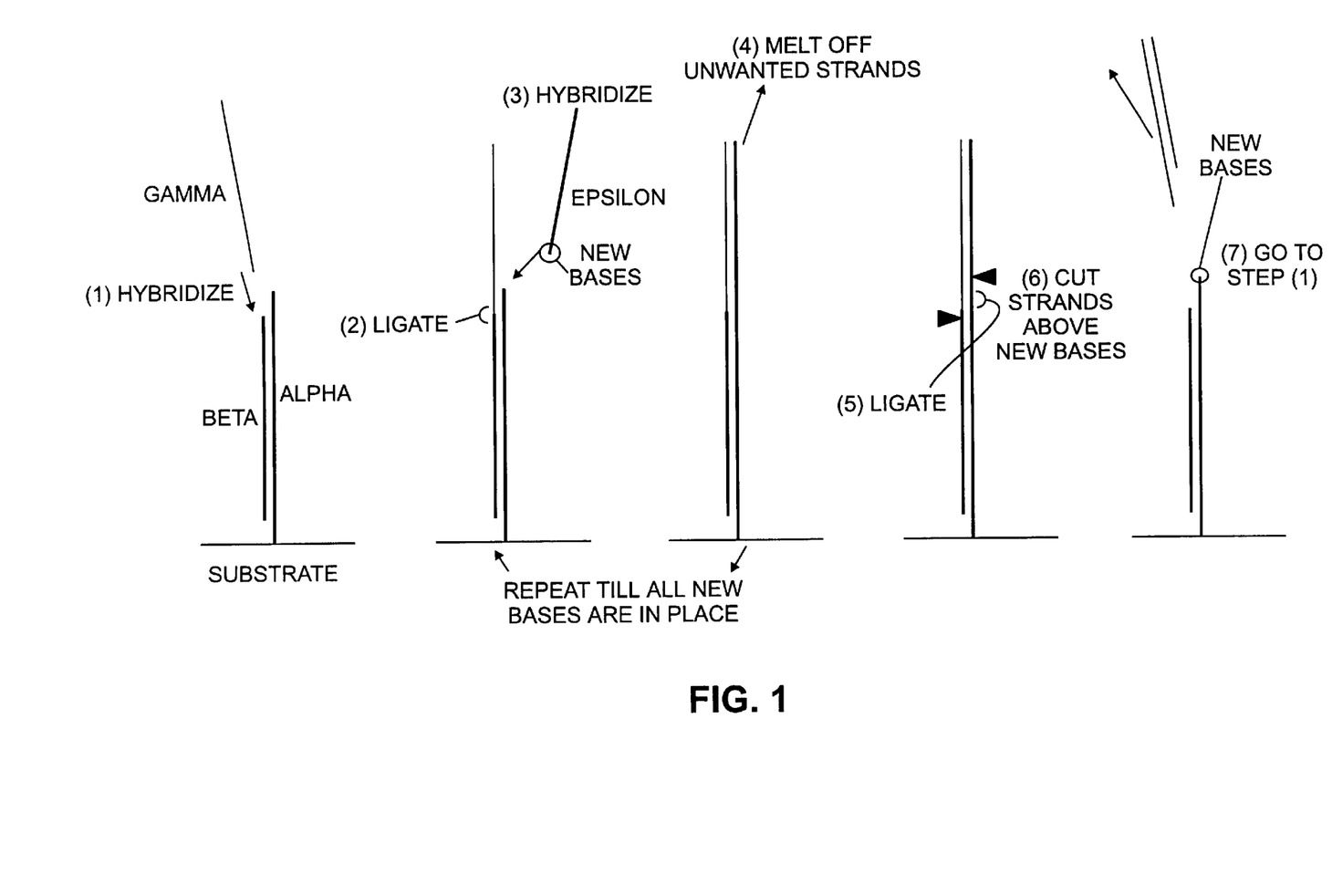
FIG. 1 illustrates the seven basic steps of the preferred form of the invention, in which the $\epsilon$ strand is hybridized to the $\gamma$ strand in step 3. These steps are described in detail in the information which follows.
Figure 2:
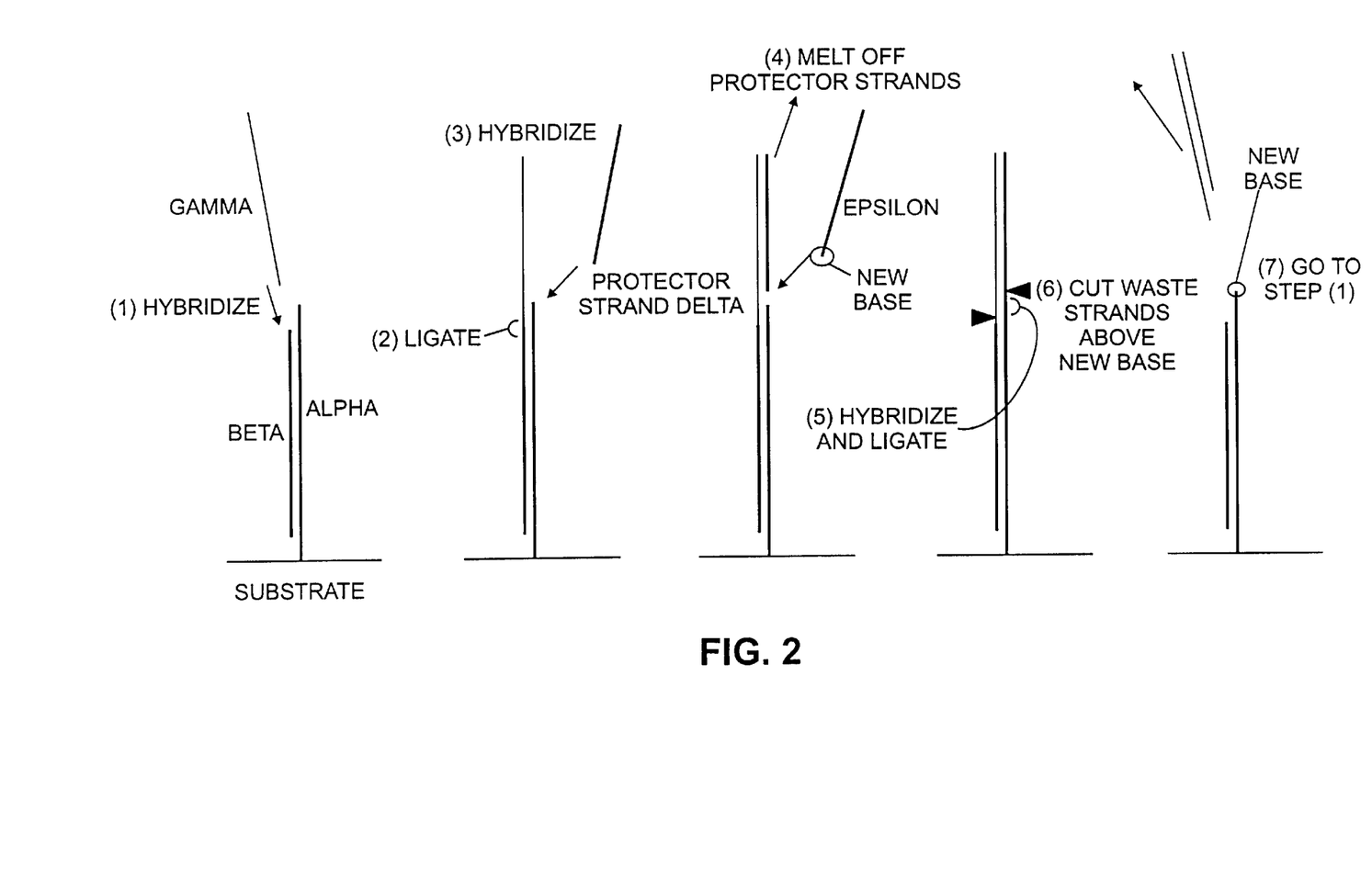
FIG. 2 illustrates an alternative method wherein protective $\delta$ strands are hybridized to the $\gamma$ strands in those portions of the DNA-covered substrate where nucleotide addition is not desired.

We start with double-stranded DNA consisting of an α strand and a complementary β strand, denoted α-β (alpha-beta). One to four or more unpaired nucleotides at the phosphorylated 5' end of the α strand extend beyond the 3'-hydroxyl-terminated end of the complementary β strand as a single-stranded structure that is referred to as a "sticky end," because it can hybridize to another single-stranded nucleic acid having a complementary nucleotide sequence. The sticky 5' ends of the α strands are the sites where new nucleotides are added to the desired oligonucleotides being synthesized. Alternatively, the orientation of the strands of the duplex α-β oligomer with respect to the sticky end may be reversed, although suitable restriction enzymes needed in the nucleotide addition step discussed below are more rare in this case. New nucleotides may be added to the duplex α-β oligomers in a reaction in which the α-β oligomers are free in solution, or are attached to a substrate as shown in FIGS. 1 and 2. In a one embodiment, a substrate is uniformly covered with duplex α-β oligomers, the DNA-covered surface is divided into local regions referred to as pixels, and a different polynucleotide sequence is synthesized in each pixel. The duplex α-β DNA molecules are attached to the substrate using known protocols involving covalent attachment of the DNA to functionalized SiO groups, attachment of biotinylated DNA to a streptavidin-coated surface, or attachment of thiolated DNA to a gold- (Au-) containing substrate. Heating of the DNA oligomers of the claimed invention may be achieved by any suitable means in accord with the types of polynucleotides being synthesized and the embodiment of the invention being employed. Heating in a heated water bath or a heat block, by an electrical circuit containing heating elements positioned at desired locations, or by electromagnetic irradiation, e.g., by laser light, is within the scope of the invention. In the case where the DNA is attached to a substrate, it is preferred that the α strand of the duplex α-β DNA oligomer be anchored to the substrate at its 3' end; however, the orientation of the strands of the duplex α-β oligomer with respect to the substrate may be reversed, although suitable restriction enzymes needed in step 6 below are more rare in this case, as noted above. Synthesis of a different polynucleotide sequence in each pixel is achieved by a sequential series of hybridization, ligation, melting, and cleaving reaction, in which each pixel is locally heated in turn so that ε (epsilon) DNA strands comprising the new nucleotides to be added hybridize only to DNA strands of the pixel where addition is to occur. The temperature for heating is selected, with consideration to the lengths and sequences of the oligomers and to the ionic strength of the reaction solution, to rapidly melt off undesired DNA strands bound to the γ strands without melting the α-β duplex structures, so that the desired ε strands with the nucleotides to be added can hybridize to the exposed γ strands.

The synthesis of DNA strands according to the invention is illustrated as follows, referring to FIGS. 1 and 2 in disclosed embodiments in which the duplex α-β oligomers are attached to and uniformly cover a substrate. One possible substrate is comprised of a wafer of Si covered by (1) a thermally-insulating 1 µm thick layer of $SiO_2$, (2) a heat absorbing 0.5 µm thick layer of amorphous Si and (3) a 0.5 µm thick layer of $SiO_2$ upon which to anchor the DNA oligomers. The substrate may be patterned into 10 µm×10 µm pads to better define the identifiable areas (pixels) of the plate. The α strand of the duplex α-β DNA oligomer is anchored to the substrate at its 3' end, and one to four or more unpaired nucleotides at its phosphorylated 5' end extend beyond the 3'-hydroxyl-terminated end of the complementary β strand to form a sticky end. To heat a single pixel to about 70° C. during the process of locally melting double-stranded DNA duplexes on a substrate will require roughly 10 milliwatts of Ar laser light (488 nm); thus approximately 1 W of Ar laser light (488 nm) would be needed to locally melt double-stranded DNA duplexes in a 100 pixel area. The Si substrate could be replaced with a sapphire substrate to allow back illumination of the desired pixels, thus protecting the DNA from direct exposure to the laser radiation. Steps of hybridization, ligation, heating to melt desired portions of the duplex DNA complexes, and cleavage by restriction enzyme, are carried out in suitable buffered solutions for these reactions which are well known to those skilled in the art (see Sambrook et al. and the other previously cited references teaching biochemical and molecular biological methodology). In embodiments in which DNA molecules are synthesized on a substrate, the DNA-covered substrate is immersed in suitable buffer during each reaction step of the method.

Step (1): A set of single-stranded γ (gamma) DNA oligomers is prepared having phosphorylated 5' ends, and in which the nucleotide sequences at the 5' ends are randomly varied so that individual members of the set of γ strands can hybridize with every possible α strand sticky end. The set of γ oligomers is allowed to hybridize with the 5' sticky ends of the α strands. The bases of a number p of nucleotides in each γ strand adjacent to the randomized 5'-terminal nucleotides are universal bases, where p is the number of new nucleotides to be transferred from the ε strands to the ends of the α strands. In theory, p can range in value from 1 to as large a number as desired. In using the invention to make a set of long polynucleotides which differ from each other at only one or a few nucleotides, it may be practical to use oligomers having large p, so as to add large blocks of nucleotides to the ends of the α strands in a single step. In using the invention to make an array of highly variable polynucleotides, the upper value of p is limited by the practical need to repeat the steps for adding p nucleotides up to $4^p$ different times for each set of p nucleotides that are added.

Step (2): In the presence of T4 DNA ligase and ATP, the 5' ends of the γ strands become ligated to the 3' ends of the β strands.

Step (3): Desired strands ε (epsilon) are introduced to hybridize to the γ strands, wherein the ε strands have p nucleotides at their 3' ends which are to be added to the α strands. Since there are $4^p$ different types of ε strands, p being the number of bases added in each step, with each different ε strand ending in one of the $4^p$ possible sets of p bases, this step would need to be repeated once for each of the different p-tuples of bases added to the entire substrate or plate, prior to ligating. The ε strands hybridize with the γ strands, with the p bases to be added pairing with the p universal bases on the γ strands. The overall lengths and nucleotide sequences of the γ and ε oligomers are selected so that γ and unligated ε strands form a duplex structure that melts at a temperature at which the α-β duplexes remain intact. A preferred configuration for the α-β-γ-ε complex is one wherein the 5' ends of ε strands and 3' ends of γ strands form blunt ends.

Step (4): In the case where a single type of polynucleotide is being made, nicks between the 3' hydroxyl terminations of the ε strands and the 5' phosphate terminations of the α strands are ligated according to Step 5 below.

In the case where an array of different substrate-bound polynucleotides is being synthesized, with new nucleotides also being added to the ends of DNA polynucleotides at other locations on the substrate, the undesired ε strands are removed by local heating without melting the α-β duplex portions, for example, by using laser illumination patterned with a lithographic mask, and are washed away. Desired ε strands are then hybridized to exposed γ strands of substrate-bound DNA molecules at the heated locations, by repeating Step 3. Steps 4 and 3 of heating to selectively remove undesired ε strands, and then hybridizing desired ε strands at each location where nucleotides are to be added, are repeated until all locations where nucleotides to be added to the sticky ends of the substrate-bound DNA have been treated.

Step (5): After all desired ε strands are hybridized to the growing DNA molecules, nicks between the 3' hydroxyl terminations of the ε strands and the 5' phosphate terminations of the α strands are ligated using T4 DNA ligase again.

Step (6): The resulting double-stranded DNA molecules are cut with a restriction enzyme that leaves a new sticky end similar to the original α-β sticky end, except that cleavage results in addition of p new nucleotides to the 5' end of the α strand. Cleavage may also result in addition of one or more paired nucleotides to the 3' end of the β strand. In the preferred method, the restriction enzyme that is used is one that cuts at a site adjacent to, but outside of, its specific recognition sequence that is built into the ε-γ sequence, to leave the new sticky end on the growing double-stranded polynucleotide. An example of such a restriction enzyme which is suitable for use in the invention is Alw 26 I. Restriction enzyme recognition sites in the growing α-β duplex can be protected from unwanted cleavage by methylation of one or both strands at the enzyme recognition site in the α-β duplex to be protected, using the appropriate methylase enzymes, or by incorporation of a methylated nucleotide or a restriction-enzyme-inhibiting nucleotide analog, which incorporation could be carried out during synthesis of the original α-β duplex stem, or in the step wherein new bases are added to the growing duplex DNA molecule.

Step (7): The process is repeated for each new set of bases to be added to the growing duplex DNA molecules.

One can design the original α and β oligomers to comprise a recognition site for a restriction enzyme that is different from the one used in the synthetic reactions, so that the polymers can be released after synthesis, if desired.

An alternate and less-preferred procedure is illustrated in FIG. 2 in which steps 3–5 are modified to include use of protective δ strands as follows:

Step (3, modified): An excess of δ (delta) protector strands are prepared which are perfectly complementary to all of the nucleotides of the single-stranded portion of the γ strands extending from the α-β duplex, except that the δ strands comprise 3'-phosphate-terminated ends, or they lack a complementary nucleotide at their 3' ends, so that unwanted ligation of the 3' ends of the δ strands to the 5'-ends of the α strands is prevented. The excess of δ protector strands are introduced to hybridize to and protect the γ strands in non-reacting pixels from binding to nucleotide-adding ε strands.

Step (4, modified): In desired locations, the protector δ strands are melted off the γ strands by local heating, for example, by using laser illumination patterned with a lithographic mask, and are washed away. Desired strands ε (epsilon) are then introduced to hybridize to the single-stranded γ oligomers. The remaining steps of the alternate method are as described above for the method in which protector δ strands are not used. If one wants to make some of the strands shorter than normal, so that the δ strands need to be left in place during the restriction step, the strands containing a δ may be protected from cutting by methylation of the restriction enzyme recognition site on the δ strand.

The foregoing detailed description has been given for clearness of understanding only and no unnecessary limitations should be understood therefrom as modifications will be obvious to those skilled in the art.

EXAMPLE

As a concrete example for the case in which a single base is to be added to the strands in each step (i.e., p=1), the following oligomers are selected to carry out the needed reactions:

34-mer, α: 5' TCTTAACATAGGAATTTGAGGCAG-
TACGCAAAAA 3'-biotin (B)(SEQ ID NO: 1).
30-mer, β': 3' AGAATTGTATCCTTAAACTCCGTCAT-
GCGT 5' (SEQ ID NO: 2).
26-mer, β: 3' TTGTATCCTTAAACTCCGTCATGCGT 5'
(SEQ ID NO: 3).

Step (2). The set of γ DNA strands (SEQ ID NO: 4) is introduced to hybridize with the sticky ends of the α strands, and the ends of the γ DNA strands are ligated to the ends of the β strands of the anchored α-β DNA by incubating with T4 DNA ligase and ATP, giving:

```
5'                    TCTTAACATAGGAATTTGAGGCAGTACGCAAAAA 3'-B  (β)

3'TCACGTCAGAGCNNNNNTTGTATCCTTAAACTCCGTCATGCGT       5'  (γ + β)
```

17-mer, γ: 3' TCACGTCAGAGCNNNNN 5' (SEQ ID NO: 4),
wherein the first N in the 3'→5' direction is a universal base and the subsequent N's designate A, C, G, or T.
13-mer, $\epsilon_A$: 5' AGTGCAGTCTCGA 3' (SEQ ID NO: 5).
13-mer, $\epsilon_T$: 5' AGTGCAGTCTCGT 3' (SEQ ID NO: 6).
13-mer, $\epsilon_G$: 5' AGTGCAGTCTCGG 3' (SEQ ID NO: 7).
13-mer, $\epsilon_C$: 5' AGTGCAGTCTCGC 3' (SEQ ID NO: 8).

The sequence of oligomer SEQ ID NO: 2 (β') consists of 18 A-T's and 12 G-C's, chosen to minimize the number of A-T and/or G-C matches of the sequence with itself for shifts of up to ±20 bases. It is further chosen to have no more than 3 A's, T's, or G-C's in a row; no more than 2 G's or 2 C's in a row. These selections are to ensure that the strands will not form hairpins. Oligomer SEQ ID NO: 2 (β') is chosen to lack the restriction enzyme Alw 26 I recognition sequence GTCTC/CAGAG or either of the four base pair segments of that sequence. Oligomer SEQ ID NO: 1 (α) is complementary to the full sequence of β', and has in addition a quartet of A's and a biotin group at the 3' end for attaching the α's to the substrate. SEQ ID NO: 3 (β) is identical to β' except that four bases are missing from the 3' end to produce a 4-base sticky end when hybridized to α. In oligomer SEQ ID NO: 4 (γ), the first N in the 3'→5' direction is a universal base, such as 5-Nitroindole, and each of the subsequent N's are random deoxyribonucleotide bases. The concentration of any one particular version of γ will be 1/256 of the total. The ε oligomers (SEQ ID NOs:5–8) each contain one of the two single-stranded sequences from the duplex DNA Alw 26 I restriction enzyme recognition sequence, which cuts leaving the 5' sticky end indicated:

where the α strand is SEQ ID NO: 1, and the γ+β strand is SEQ ID NO: 11 wherein the first N in the 3'→5'direction in γ is a universal base and the subsequent N's designate A, C, G, or T. Step (3). The DNA-covered substrate is incubated in the presence of an oligomer denoted $\epsilon_X$ containing the base X to be added to the α strand, so that the $\epsilon_X$ oligomers hybridize to the γ strands. In this example, $\epsilon_A$=SEQ ID NO: 5; $\epsilon_T$=SEQ ID NO: 6; $\epsilon_G$=SEQ ID NO: 7; and $\epsilon_C$=SEQ ID NO: 8.

Step (4): To add one of the 4 bases A, T, G, or C, to DNAs of 4 or more different pixels, the hybridization step would need to be repeated with each of the 4 different $\epsilon_X$ strands at the desired substrate locations prior to ligating and cleaving. After the first step in which an $\epsilon_X$ strand is hybridized to the substrate-bound DNA, and before each subsequent $\epsilon_X$ addition step, undesired $\epsilon_X$ strands are melted away from the DNA of the pixels where the nucleotides are to be added by local heating, e.g., by using laser illumination patterned with a lithographic mask for 10 seconds to give a local temperature of approximately 70° C., thereby producing the same duplex DNA structure comprising a duplex α-β portion produced in Step 2, wherein γ DNA strands in the selected areas are receptive to one of the $\epsilon_X$ oligomers. Desired $\epsilon_X$ strands are then hybridized to exposed γ strands of substrate-bound DNA molecules at the heated locations by repeating Step 3. Local heating to selectively remove undesired $\epsilon_X$ strands without melting duplex α-β portions (Step 4), and hybridization of desired $\epsilon_X$ strands at each location where nucleotides are to be added (Step 3), are repeated until all

```
5' ...NNNGTCTCN      3'    (SEQ ID NO: 9, from the ε strand)

3' ...NNNCAGAGNNNNN 5'     (SEQ ID NO: 10, from the γ strand),
``` wherein the 5$^{th}$ N from the 5' end of the γ strand is a universal base, and the other Ns designate A, C, G, or T.

The detailed steps in making a DNA hybridization array are as follows.

Step (1). We start by attaching α oligomers uniformly over the substrate, e.g., by using the affinity of biotin for a streptavidin-coated glass surface, and β strands are then hybridized with the anchored α strands, giving:

pixels where nucleotides are to be added have been treated with a desired $\epsilon_X$ oligomer.

Step (5): After all desired ε strands are hybridized to the growing DNA molecules, nicks between the 3' hydroxyl terminations of the ε strands and the 5' phosphate terminations of the α strands are ligated using T4 DNA ligase again. Ligation of the hybridized $\epsilon_X$ strands to the α strands by incubating with T4 DNA ligase and ATP gives:

```
5' TCTTAACATAGGAATTTGAGGCAGTACGCAAAAA 3'-B  (α, SEQ ID NO:1)

3'      TTGTATCCTTAAACTCCGTCATGCGT      5'  (β, SEQ ID NO:3).
```

```
5' AGTGCAGTCTCGNTCTTAACATAGGAATTTGAGGCAGTACGCAAAAA   3'-B   (ϵ + α)

3' TCACGTCAGAGCNNNNNTTGTATCCTTAAACTCCGTCATGCGT       5'   (γ + β),
``` where the γ+β strand is SEQ ID NO: 11 as described above, and wherein and the ϵ+α strand is SEQ ID NO: 12
wherein N is A, C, G, or T.

Step (6): The DNA-covered substrate is incubated at 37° C. with Alw 26 I restriction enzyme, and a small sticky-ended double-stranded oligomer is cut off and washed away producing:

```
5' NTCTTAACATAGGAATTTGAGGCAGTACGCAAAAA   3'-B
(α + N)

3'      NTTGTATCCTTAAACTCCGTCATGCGT      5'
(β + N),
``` where α+N is SEQ ID NO: 13 and β+N is SEQ ID NO: 14,
wherein N is A, C, G, or T, and

```
5'  AGTGCAGTCTCG       3' (SEQ ID NO: 15)

3'  TCACGTCAGAGCNNNN   5' (SEQ ID NO: 16),
``` wherein the first N in the 3'→5' direction is a universal base and the subsequent N's designate A, C, G, or T. This leaves the new deoxyribonucleotides X of $\epsilon_X$ added to the α strands, and the α-β strands in a state precisely like that encountered in step 2, except for being one base pair longer.

Step (7): The synthetic cycle is now repeated by returning to Step 2 of the above-described example. By repeating Steps 2–6 one may now add as many bases as desired in what ever pattern is needed.

Step (8): When the α strands have the desired sequence, the lengthened β strands are melted off and washed away. The β' strands are then allowed to hybridize with the α strands, leaving the newly synthesized polynucleotides in single-strand form, attached at their 3' ends to the blunt-ended α-β duplexes at the 5' ends of the α strands. If the number of added nucleotides happens to be four, this last step is not needed.

The ϵ strands are more than 50% G-C's and would be expected to dissociate at a rate of less than $10^{-4}$ s$^{-1}$ or less at 22° C., compared to $10^2$ s$^{-1}$ at 70° C. [12]. This estimate comes from an extrapolation of the data given in FIG. 6 of Ref. 12. The melting point for similar 14-mers is about 40° C. [13]. Thus, a 10 sec heat pulse raising the temperature of a spot to 70° C. will result in a 99.9% chance that a new base is incorporated where it is wanted and a similar chance that it is not incorporated elsewhere if the temperature there is less than 20° C. The β' strands dissociate at a rate of roughly $10^{-5}$ s$^{-1}$ at 70° C., and thus the structure should be quite stable under the temperature cycling needed for Steps 2–7. The fidelity of synthesis attained using the present invention permits efficient and accurate synthesis of polynucleotides in substrate-bound arrays that are considerably longer than those that can be accurately made using current technologies; for example, polynucleotides of up to 20, 30, 50, or even 100 or more nucleotide subunits, can be accurately made by the present invention.

It is estimated that when one pixel is heated to the 70° C. required in Step 4 the temperatures of any unilluminated neighboring pixels will not rise above 20° C. if the substrate is heat-sunk to near 0° C. Although the dissociation rates for oligomers are a steep function of temperature, the borders of the pixels will contain sequences that do not correspond to the programmed growth. In operation, the area between the pixels should be either disregarded during read-out or masked by a patterned photoresist or evaporated layer.

At concentrations of $10^{-6}$ M (moles per liter), hybridization reactions rates are of the order of 1 s$^{-1}$. The rate limiting steps in this scheme are the two ligation steps and the one restriction step. According to their catalog, one New England Biolabs (NEB) unit for the T4 DNA ligase gives 50% ligation of Hind III fragments in 30 m at a 5' DNA termini concentration of $10^{-7}$ M. Using a high concentration of enzyme will result in sufficiently complete ligation in a few minutes. The restriction enzyme will also act in a few minutes. The ligation and restriction enzyme cleavage steps need to occur only once in the four cycles. One may thus estimate that growth of a DNA array by the method described would take less than 30 minutes per four bases added, comparable to the 1 hour per four bases in the early light-directed synthesis work of Ref. 7.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Each of the following citations is herein incorporated by reference:

1. R. Drmanac, I. Labat, I. Brukner and R. Crkvenjakov, "Sequencing of megabase plus DNA by hybridization: theory of the method", *Genomics* 4, 114–128 (1989).
2. E. L. Sheldon, et al., "Matrix DNA hybridization", *Clinical Chemistry* 39, 718-719 (1993).
3. M. Chee, et al., "Accessing genetic information with high-density DNA arrays", *Science* 274, 610–614 (1996).
4. M. J. Kozal et al., "Extensive polymorphisms observed in HIV-1 clade B protease gene using high-density oligonucleotide arrays", *Nature Medicine* 2, 753–759 (1996).
5. D. I. Stimpson et al., "Real-time detection of DNA hybridization and melting on oligonucleotide arrays by using optical wave guides", *Proc. Nat. Acad. Sci. USA* 92, 6379–6383 (1995).
6. S. P. A. Fodor, J. L. Read, M. C. Pirrung, L. Stryer, A. T. Lu and D. Solas "Light-directed, spatially addressable parallel chemical synthesis", *Science* 251, 767–773 (1991).
7. A. C. Pease, D. Solas, E. J. Sullivan, M. T. Cronin, C. P. Holmes and S. P. A. Fodor, "Light-generated oligonucleotide arrays for rapid DNA sequence analysis", *Proc, Nat. Acad. Sci. USA* 91, 5022–5026 (1994).
8. G. H. McGall, S. P. A. Fodor and E. L. Sheldon, "Spatially-addressable immobilization of oligonucleotides and other biological polymers on surfaces", U.S. Pat. No. 5,412,087 (May 2, 1995).

9. G. McGall, J. Labadie, P. Brock, G. Wallraff, T. Nguyen and W. Hinsberg, "Light-directed synthesis of high-density oligonucleotide array using semiconductor photoresists", *Proc. Nat. Acad. Sci. USA* 93, 13555–13560 (1996).
10. R. Nichols, P. C. Andrews, P. Zhang and D. E. Bergstrom "A universal nucleoside for use at ambiguous sites in DNA primers", *Nature* 369, 492-493 (1994).
11. D. Loakes and D. M. Brown, "5-Nitroindole as an universal base analogue", *Nucleic Acids Research* 22, 4039–4043 (1994).
12. L. E. Morrison and L. M. Stols, "Sensitive fluorescence-based thermodynamic and kinetic measurements of DNA hybridization in solution", *Biochemistry* 32, 3095–3104 (1993). See also C. R. Cantor and P. R Schimmel, *Biophysicial Chemistry* (Freeman, N.Y., 1980) p. 1217.
13. R. B. Wallace, J. Shaffer, R. F. Murphy, J. Bonner, T. Hirose and K. Itakura, "Hybridization of synthetic oligodeoxyribonucleotides to $\phi_X$ 174 DNA: the effect of a single base pair mismatch", *Nucleic Acids Research* 6, 3543–3557 (1979).
14. L. M. Adleman, "Molecular computation of solutions to combinatorial problems", *Science* 266, 1021–1023.
15. M. C. Pirrung, J. L. Read, S. P. A. Fodor and L. Stryer, "Large scale phase synthesis of polypeptides and receptor binding screening thereof", U.S. Pat. No. 5,143,854 (Sep. 1, 1992).
16. G. H. McGall et al., "The efficiency of light-directed synthesis of DNA arrays on glass substrates," *Journal of the American Chemical Society*, 119, 5081–5090 (1997).

What is claimed is:

1. A method for synthesizing a polynucleotide comprising the following steps:
    a) obtaining a double-stranded polynucleotide wherein one or more nucleotides at one end of one strand ($\alpha$) extend as a single-stranded structure beyond the end of the other ($\beta$) strand to form a sticky end;
    b) obtaining a third polynucleotide strand ($\gamma$) which has a nucleotide sequence at one end which can hybridize to the sticky end of the $\alpha$ polynucleotide, wherein the bases of a number p of nucleotides in the $\gamma$ strand adjacent to the terminal nucleotide sequence complementary to the sticky end of the $\alpha$ strand are universal bases, where p is a number of new nucleotides to be added to the end of the $\alpha$ strand,
    hybridizing the $\gamma$ strand to said sticky end, and ligating the hybridized end of the $\gamma$ strand to the end of the $\beta$ strand;
    c) obtaining a fourth polynucleotide strand ($\epsilon$) which is complementary to the single-stranded portion of the ligated $\gamma$ strand, wherein the $\epsilon$ strand has p nucleotides at its end which are to be added to the $\alpha$ strand, which nucleotides pair with the p universal bases of the $\gamma$ strand and
    hybridizing the $\epsilon$ strand to the $\gamma$ strand, and ligating the end of the hybridized $\epsilon$ strand to the adjacent end of the $\alpha$ strand;
    d) cutting the resulting double-stranded DNA complexes with a restriction enzyme so that the end of the $\alpha$ strand has p bases more than it had in step a, and so that one or more nucleotides of the lengthened end of the $\alpha$ strand extend beyond the end of the $\beta$ strand to form a sticky end; and
    e) repeating steps b–d until the newly synthesized polynucleotide has the desired nucleotide sequence.

2. The method of claim 1 wherein the polynucleotide to be synthesized, and each of the $\alpha$, $\beta$, $\gamma$, and $\epsilon$ polynucleotides, are DNA.

3. The method of claim 1 wherein the 5' end of the $\alpha$ strand is phosphorylated, the 3' end of the $\beta$ strand terminates in a hydroxyl group, and one or more nucleotides at the 5' end of the $\alpha$ strand extend beyond the 3' end of the $\beta$ strand to form a sticky end;
    wherein the bases of the $\gamma$ strand which hybridize to the sticky end of the $\alpha$ strand are at the 5' end of the $\gamma$ strand, and the 5' end of the $\gamma$ strand is ligated to the 3' end of the $\beta$ strand;
    wherein the p bases of the $\epsilon$ strand which are to be added to the polynucleotide are at the 3' end of the $\epsilon$ strand, and the 3' end of the $\epsilon$ strand is ligated to the 5' end of the $\alpha$ strand;
    and wherein cutting with the restriction enzyme results in addition of the p nucleotides to the 5' end of the $\alpha$ strand.

4. The method of claim 1 wherein the specific recognition sequence of the restriction enzyme is present in the $\epsilon$-$\gamma$ sequence, and the restriction enzyme is one which cuts at a site adjacent to, but outside of, its specific recognition sequence, on that side of the recognition sequence which comprises the double-stranded $\alpha$-$\beta$ polynucleotide.

5. The method of claim 4 wherein the restriction enzyme is Alw 26 I.

6. The method of claim 1 wherein the $\alpha$ strand comprises the sequence set forth in SEQ ID NO: 1, and the $\beta$ strand comprises the sequence set forth in SEQ ID NO: 3.

7. The method of claim 1 wherein the $\gamma$ strand comprises the sequence set forth in SEQ ID NO: 4, and $\epsilon$ strand comprises a sequence selected from the group consisting of SEQ ID NO: 5, SEQ ID NO: 6, SEQ ID NO: 7, and SEQ ID NO: 8.

8. The method of claim 1 wherein the universal base is 5-Nitroindole.

9. The method of claim 1 wherein one or more of said of $\alpha$, $\beta$, $\gamma$, and $\epsilon$ polynucleotides comprises at least one modification selected from the group consisting of a modified internucleotide linkage, a deoxynucleotide analog, a ribonucleotide analog, or a base-pairing, non-nucleotide subunit.

10. The method of claim 1 wherein the α strand is anchored to a substrate.

11. The method of claim 10 wherein the substrate is a Si or sapphire wafer covered by a first layer of $SiO_2$, a second layer of amorphous Si, and a third layer of $SiO_2$.

12. The method of claim 11 wherein the α strand is anchored to the substrate by covalent attachment of the DNA to functionalized SiO groups.

13. The method of claim 10 wherein the substrate comprises a streptavidin-coated glass surface, and wherein the α strand is biotinylated at one end, so that binding of the biotin moiety to one of said streptavidin molecules anchors the α strand to the substrate.

14. The method of claim 10 wherein the 3' end of the α strand is attached to the substrate.

15. The method of claim 1 wherein the newly synthesized polynucleotide attached to the 5' end of the original α strand comprises 10–100 or more nucleotide subunits.

16. A method for making an article for nucleic acid hybridization comprising a substrate-bound array of hybridizing polynucleotides that have different, selected nucleotide sequences, the method comprising the steps of:

a) covering part or all of a substrate with double-stranded polynucleotides comprising complementary α and β polynucleotide strands hybridized to each other, wherein the 3' ends of the α strands are anchored to the substrate and the 5' ends of the α strands are unanchored and phosphorylated, wherein the 3' end of each β strand terminates in a hydroxyl group, and wherein one or more nucleotides at the 5' end of each α strand extend as a single-stranded structure beyond the 3' end of the β strand to form a sticky end;

b) hybridizing to said sticky ends a third polynucleotide strand (γ) which has a nucleotide sequence at its 5' end which is complementary to the sticky end of the α strand, wherein the bases of a number p of nucleotides in the γ strand adjacent to said terminal nucleotide sequence complementary to the sticky end of the α strand are universal bases, where p is a number of new nucleotides to be added to the end of each α strand, and ligating the hybridized 5' ends of the γ strands to the adjacent 3' ends of the β strands;

c) hybridizing to said γ strands a fourth polynucleotide strand (ε) which is complementary to the single-stranded portion of each ligated γ strand, wherein each ε strand has p nucleotides at its 3' end which are to be added to the 5' end of an α strand, which nucleotides pair with the p universal bases on each γ strand;

d) locally heating those pixels on the substrate where a different selected sequence of p nucleotides is to be added, to remove the undesired ε strands from the ligated γ strands in those pixels;

e) hybridizing to the single stranded γ strands in the heated pixels ε strands which have at their 3' ends a selected sequence of p nucleotides which is different from the sequence of p nucleotides added previously;

f) repeating steps d and e until ε oligomers with desired sequences have been hybridized to all pixels where nucleotides are to be added;

g) ligating the 3' ends of the hybridized ε strands to the adjacent 5' ends of the α strands;

h) cutting the resulting double-stranded DNA complexes with a restriction enzyme so that the end of each α strand has p bases more than it had in step a, and so that one or more nucleotides of the lengthened 5' end of the α strand extend beyond the 3' end of the β strand to form a new sticky end; and e) repeating steps b–h until the polynucleotides in each pixel on the substrate have the desired nucleotide sequence.

17. The method for making an article for nucleic acid hybridization of claim 16, wherein the step of locally heating pixels on the substrate to remove previously hybridized ε strands from the γ strands in those pixels comprises using laser illumination patterned with a lithographic mask.

18. The method of claim 16 wherein the hybridizing polynucleotides that are synthesized are DNA.

19. The method of claim 16 wherein the specific recognition sequence of the restriction enzyme is present in the ε-γ sequence, and the restriction enzyme is one which cuts at a site adjacent to, but outside of, its specific recognition sequence, on that side of the recognition sequence which comprises the double-stranded α-β polynucleotide.

20. The method of claim 19 wherein the restriction enzyme is Alw 26 I.

21. The method of claim 16 wherein the α strand comprises the sequence set forth in SEQ ID NO: 1, and the β strand comprises the sequence set forth in SEQ ID NO: 3.

22. The method of claim 16 wherein the γ strand comprises the sequence set forth in SEQ ID NO: 4, and ε strand comprises a sequence selected from the group consisting of SEQ ID NO: 5, SEQ ID NO: 6, SEQ ID NO: 7, and SEQ ID NO: 8.

23. The method of claim 16 wherein the universal base is 5-Nitroindole.

24. The method of claim 16 wherein one or more of said of α, β, γ, and ε polynucleotides comprises at least one modification selected from the group consisting of a modified internucleotide linkage, a deoxynucleotide analog, a ribonucleotide analog, or a base-pairing, non-nucleotide subunit.

25. The method of claim 16 wherein the α strand is anchored to a substrate which is a Si or sapphire wafer covered by a first layer of $SiO_2$, a second layer of amorphous Si, and a third layer of $SiO_2$.

26. The method of claim 16 wherein the α strand is anchored to the substrate by covalent attachment of the DNA to functionalized SiO groups.

27. The method of claim 16 wherein the substrate comprises α streptavidin-coated glass surface, and wherein the α strand is biotinylated at one end, so that binding of the biotin moiety to one of said streptavidin molecules anchors the α strand to the substrate.

28. The method of claim 16 wherein the newly synthesized polynucleotides attached to the 5' ends of the original α strands comprise 10–100 or more nucleotide subunits.

* * * * *

```
                              SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:1:

TCTTAACATA GGAATTTGAG GCAGTACGCA AAAA                                   34

(2) INFORMATION FOR SEQ ID NO:2:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:2:

TGCGTACTGC CTCAAATTCC TATGTTAAGA                                        30

(2) INFORMATION FOR SEQ ID NO:3:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:3:

TGCGTACTGC CTCAAATTCC TATGTT                                            26

(2) INFORMATION FOR SEQ ID NO:4:

(i) SEQUENCE CHARACTERISTICS:
             (A) LENGTH: 17 base pairs
             (B) TYPE: nucleic acid
```

(C) STRANDEDNESS: single
        (D) TOPOLOGY: linear (ii) MOLECULE TYPE: DNA (xi) SEQUENCE DESCRIPTION: SEQ ID NO:4:

NNNNNCGAGA CTGCACT                                                    17

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AGTGCAGTCT CGA                                                        13

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AGTGCAGTCT CGT                                                        13

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AGTGCAGTCT CGG                                                        13

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AGTGCAGTCT CGC                                                        13

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

NNNGTCTCN                                                              9

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

NNNNNGAGAC NNN                                                         13

(2) INFORMATION FOR SEQ ID NO:11:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TGCGTACTGC CTCAAATTCC TATGTTNNNN NCGAGACTGC ACT                         43

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AGTGCAGTCT CGNTCTTAAC ATAGGAATTT GAGGCAGTAC GCAAAAA                     47

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

NTCTTAACAT AGGAATTTGA GGCAGTACGC AAAAA                                  35

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGCGTACTGC CTCAAATTCC TATGTTN                                           27

-continued (2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:15:

AGTGCAGTCT CG                                                                          12

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:16:

NNNNCGAGAC TGCACT                                                        16